United States Patent [19]

Hamilton et al.

[11] 4,044,756

[45] Aug. 30, 1977

[54] PHOSPHENE GENERATOR DEVICE

[76] Inventors: Robert W. Hamilton, 5109 Williams Fork Trail; No. 207, Boulder, Colo. 80301; Robert E. Gillis, P.O. Box 67, Aptos, Calif. 95003

[21] Appl. No.: 673,145

[22] Filed: Apr. 2, 1976

[51] Int. Cl.² .................... A61B 5/00; G02B 11/04; G03B 35/02
[52] U.S. Cl. .................................... 128/2 N; 352/63; 350/273
[58] Field of Search ............ 128/2 N, 1 C, 2 T, 25 A; 352/63, 57; 350/266, 268, 271, 273, 275

[56] References Cited

U.S. PATENT DOCUMENTS

| 2,825,263 | 3/1958 | Dockhorn | 352/63 |
| 3,970,371 | 7/1976 | Kaiwa et al. | 350/273 |

Primary Examiner—Stephen C. Pellegrino
Attorney, Agent, or Firm—John E. Reilly

[57] ABSTRACT

A device for generating phosphenes is adapted to be worn on the head of a person and is provided with eye openings to pass light from an external light source to the eyes. A rotating element modulates the light passing through the eye opening by being sized and selectably rotated so as to create high intensity phosphenes.

11 Claims, 8 Drawing Figures

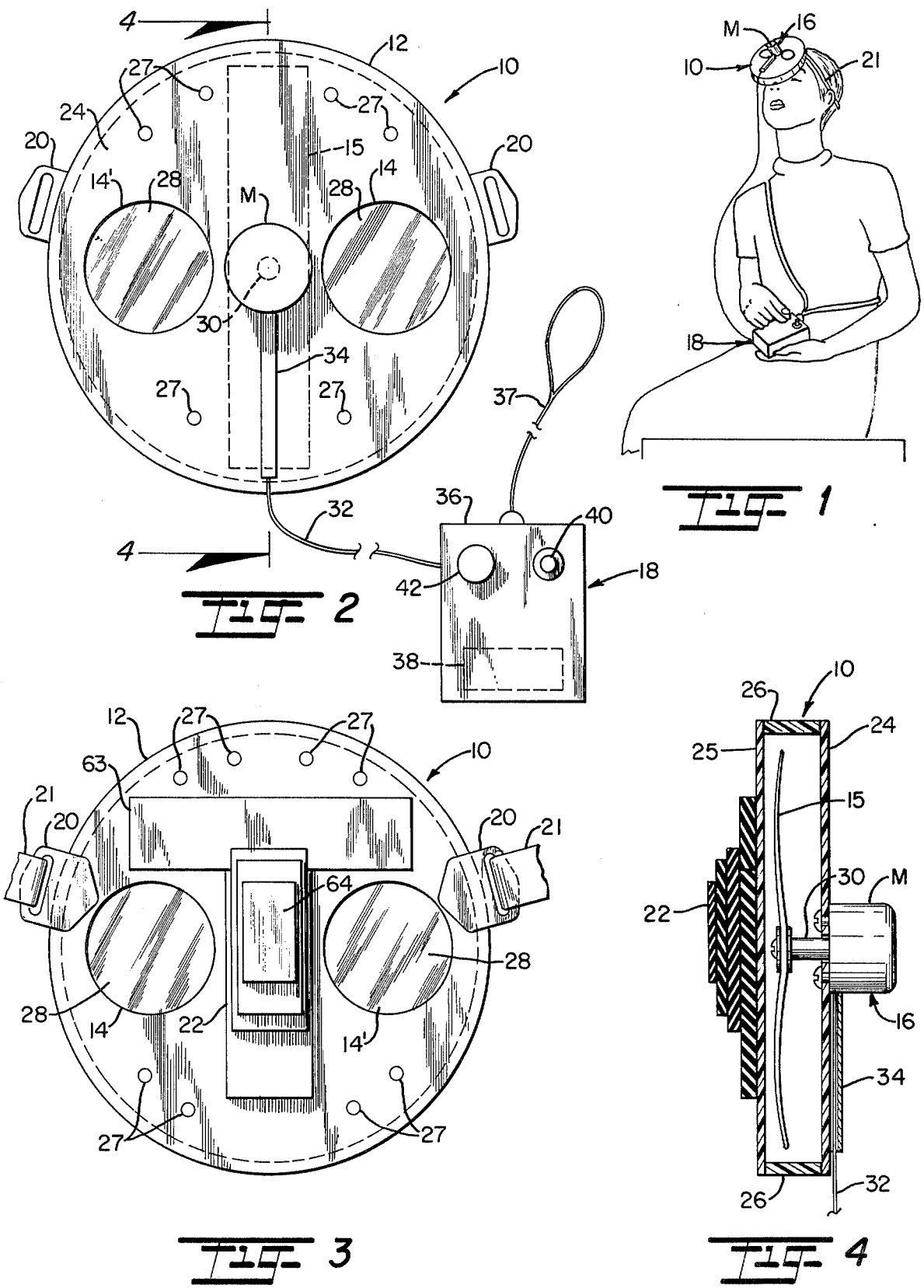

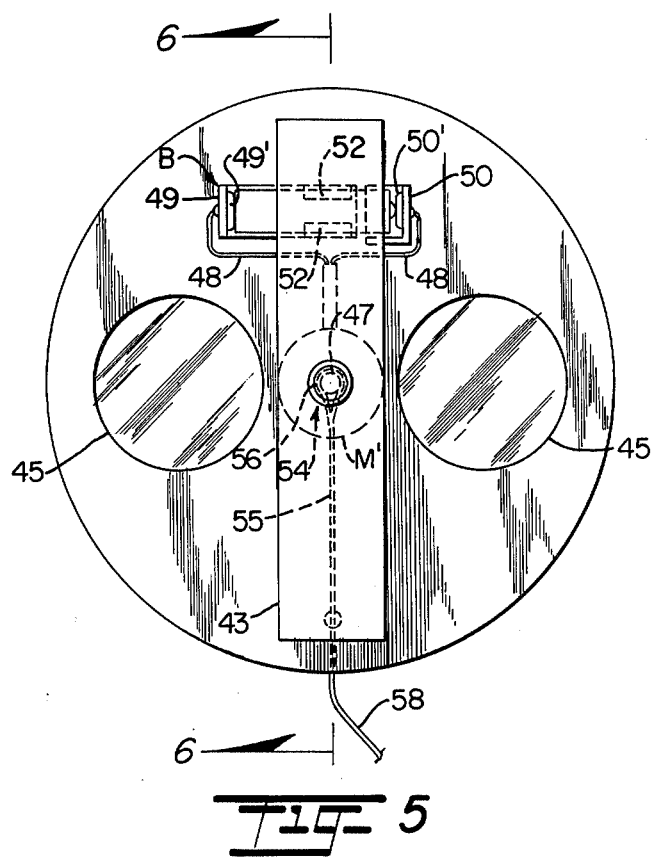
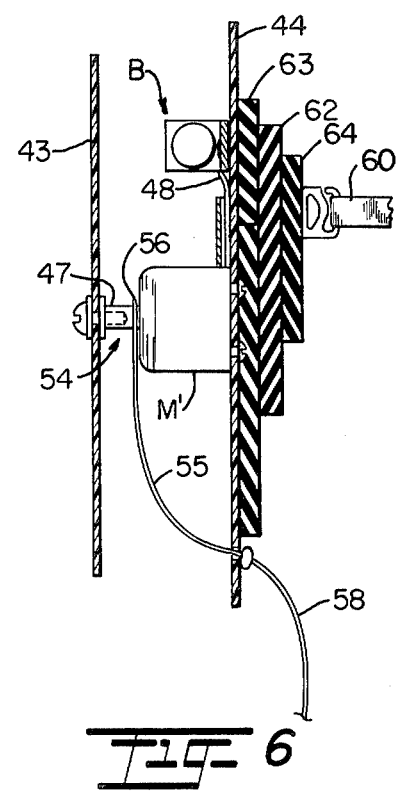
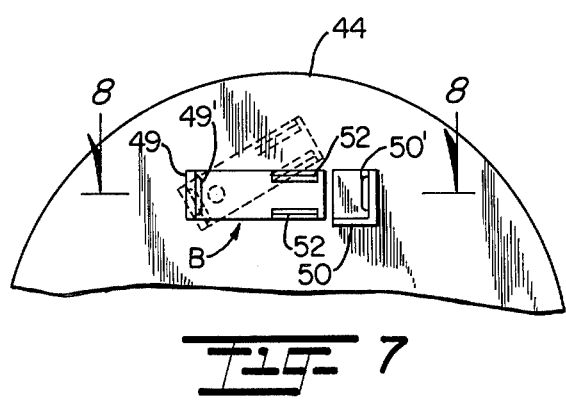
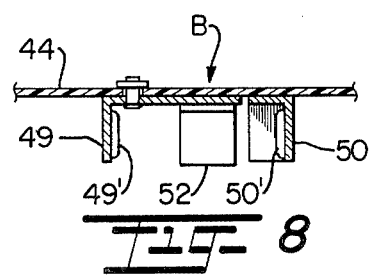

PHOSPHENE GENERATOR DEVICE

This invention relates to a novel and improved phosphene generating unit and more particularly relates to a novel and improved method and apparatus capable of modulating a high intensity, external light source at a predetermined frequency and wave form whereby to create unique visual impressions of light, color or pattern.

BACKGROUND OF THE INVENTION

Subjective images and impressions of light, color or pattern generated within the eyes and brain rather than by optical images from outside are commonly termed "phosphenes" and can be formed in various ways. For example, strobe light or electrical pulses applied to the scalp or eyes, or fluctuating magnetic fields in the vicinity of the brain can create such impressions. Furthermore, pressure on the eye, a blow to the brain or direct electrical impulses may cause similar experiences. Generation of such phosphenes may range from simple one-color flashes to multicolored, complex visual patterns, such as, snow flakes, diamonds, whorls, checks or stripes of various colors or hues in addition to many forms and colors that the imagination might create. In general the patterns would not appear to have any direct relation to the shape or the pattern of the light source or force creating them in the mind and therefore do not appear to be representative of the source which evokes such patterns. It has been theorized that the patterns of phosphenes may be related to the geometry of the eye or brain; and when intentionally evoked may take on as many forms or colors as the imagination might create particularly by constant practice.

Devices which have been developed for producing phosphenes have suffered from a number of defects: Principally, known devices have not taken into consideration the most desirable or optimum conditions for maximizing phosphene generation or reaction while at the same time minimizing flicker sickness. In order to optimize phosphene generation using a strobe light, the maximum average intensity of light must be achieved without reaching pear brightness levels which could be damaging to the eye and the frequency of the pulses must be below the flicker fusion frequency. Generally, the apparent brightness of light falling on the eyes is an average of the light passed over a sampling period roughly equal to the flicker fusion frequency (i.e.: the minimum frequency produced by a flashing light which is necessary to insure continuous visual sensation). As a result, phosphene generators which employ light pulses of relatively short duration in relation to the duration of darkness would require extremely or intensely bright light pulses and at a level of brightness which could be damaging to the eye. The German patent to Sownberger No. 866,905 granted in 1953 discloses a stereoscopic device in which light from an external source has been converted into light pulses of relatively short duration by alternately blocking the passage of light to the eye by placing a rotatable slotted member in front of the eyes and rotating about an axis perpendicular to the passage of light. Other rotating slot devices representative of the prior art are shown in United States Letters Patent to Jarrow U.S. Pat. No. 2,387,758, Denecke U.S. Pat. No. 3,049,962 and Neasham U.S. Pat. No. 3,415,598 as well as British Patent to Bankl No. 012,797 and the French Patent to Georges et al No. 1,297,887. Further, various types of stereoscopic viewers containing light modulating features which operate with motor drives and switching frequencies above the flicker fusion frequency and, for instance, are shown in U. S. Letters Patent to Dockhorn U.S. Pat. Nos, 2,810,318; 3,825,263, and 2,825,264 as well as Kratomi U.S. Pat. No. 3,737,567. None of the foregoing discloses or contemplates an arrangement wherein maximum average light intensity is achieved while minimizing flicker sickness in the manner devised according to the present invention and specifically through a unique manner and means by which the size and speed of a rotating, oscillating or reciprocating element in front of the eyes are so correlated and coordinated as to produce optimum, safe conditions for phosphene generation in a simplified dependable manner.

SUMMARY OF THE INVENTION

It is therefore an object of the present invention to provide for a novel and improved phosphene generator which is operative to produce alternate light and dark pulses within the optimum range for phosphene generation without exceeding the safety level of the light.

Another object is to provide a method and apparatus for phosphene generation which is lightweight, portable and capable of variably controlling the frequency and duration of light pulses for conversion into phosphenes perceived by the wearer in a novel, safe manner.

It is a further object of the present invention to provide a novel and improved phosphene generator which will minimize a tendency to cause flicker sickness and can be safely used by persons of all ages.

In accordance with the present invention, a phosphene generator unit is adapted to be worn on the head with openings therein aligned with the eyes so as to pass light to the eyes from an external source. A movable element preferably in the form of a rotatable propeller blade is caused to traverse the openings in such a way as to produce alternating light and dark pulses of a predetermined frequency, and the movable element is sized so as not to completely block the eye openings in passing thereacross so as to avoid production of completely dark pulses and maintain maximum average light intensity within a safe range or level for the eyes. Preferably the speed of movement of the movable element is controlled by a variable speed motor drive in order to permit variations in the patterns and other characteristics of the phosphenes generated and to permit close control of such variations by the wearer.

In its preferred form, the phosphene generator may consist of a plate or housing supported by a cushion on the forehead of the wearer and includes eye openings in the plate or housing which are aligned to pass light from an external light source. The movable element is centered on the plate or so disposed in the housing as to be movable at a controlled frequency across the eye openings so as to selectively but not completely block the passage of light through the openings; and as stated the movable element is preferably formed of a propeller blade which is controlled by a variable speed motor drive. In the alternative, a constant speed motor or other drive means may be employed to rotate the propeller with a manually controlled braking element associated with the propeller to control its speed of rotation.

Other objects, advantages and capabilities of the present invention will become more apparent as the description proceeds, taken in conjunction with the accompanying drawings, in which:

BRIEF DESCRIPTION OF THE DRAWINGS

FIG. 1 is a perspective view of one embodiment of phosphene generator device formed in accordance with the present invention and shown in position for use.

FIG. 2 is a front view in elevation of the phosphene generator device shown in FIG. 1.

FIG. 3 is a rear view of the form of invention illustrated in FIG. 1.

FIG. 4 is a cross-sectional view taken about lines 4—4 of FIG. 2.

FIG. 5 is a front view in elevation of a modified form of the present invention.

FIG. 6 is a cross-sectional view of the modified form of invention shown in FIG. 5.

FIG. 7 is a fragmentary view in detail of the removable battery pack employed in the form shown in FIGS. 1 to 4; and FIG. 8 is a cross-sectional view taken about lines 6—6 of FIG. 5.

DETAILED DESCRIPTION OF THE PREFERRED EMBODIMENT

Now referring in detail to the drawings, there is shown by way of illustrative example in FIGS. 1 to 4 a phosphene generator device 10 broadly comprised of a housing 12 provided with aligned pairs of front and rear horizontally spaced eye openings 14 and 14', a movable light control member 15, motor drive means M and a remote speed control 18. The housing includes attaching members 20 on opposite sides for a head strap 21, and a cushion member 22 is affixed to the rear surface of the housing so that when the device is placed over the head of a person in the manner illustrated in FIG. 1, the cushion member 22 will rest against the forehead and bridge of the nose.

As a preliminary to a more detailed discussion of the combination of elements comprising the device 10, generally, the movable light control member 15 is adapted to be rotated at a predetermined speed so as to intercept light from an external source passing through the eye openings 14 and 14' whereby to convert the light into alternate light and dark pulses, the speed of rotation being such as to cause development of light pulses at a rate or frequency in the range of one to 25 cycles per second. Moreover, the movable light control member is sized so as not to completely block the eye openings 14 and 14' at any one time thereby assuring that there is never any complete interruption of light whereby to avoid generating completely dark pulses which has been discovered to be a major cause of flicker sickness. Moreover, the movable element 15 is sized in relation to its speed of rotation so as to generate light pulses of relatively long duration with respect to the period of darkness pulses so as to maximize the average intensity of light within the safe range of light intensity to the human eye. Accordingly, rotation or other movement of the movable light control member 15 about an axis parallel to the path of light through the eye openings so as not to completely block light passage optimizes phosphene generation by producing relatively long duration light pulses within the safe level of light permitted by the human eye, all as hereinafter discussed in more detail.

Considering in more detail the construction and arrangement of elements as illustrated in FIGS. 1 to 4, the housing 12 is preferably composed of front and rear circular face plates 24 and 25 permanently secured together in spaced relation to one another by an outer peripheral band or ring 26, and a plurality of vent openings 27 are provided in the plates 24 and 25. The eye openings 14 and 14' formed in each of the face plates 24 and 25 are correspondingly formed so as to be horizontally spaced on opposite sides of center a distance corresponding to the spacing between the eyes with front and rear openings 14 and 14' aligned with one another so as to permit direct passage of light through the housing. Additionally, the front or rear eye openings 14 or 14', or a combination of both, preferably are fitted with a lens or filter 28 to insure that the maximum safe level of light passing through the eye openings is not exceeded. Additionally, each eye opening is sized to be on the order of 1½ inches to assure that the eye is fully exposed to light notwithstanding slight differences in eye spacing when worn by different individuals and further to assure that the eye openings are properly sized in relation to the size and width of the movable light control member 15.

The movable light control member 15 is preferably in the form of a propeller having a single blade normal to its center axis and fixed for rotation about a central drive shaft 30. The blade is of a length to extend beyond the outermost edges of the eye opening and may be slightly twisted so as to generate an air current through the vent holes 27. In this relation, the blade may be composed of various materials such as from a plastic foam or other resilient material which will have sufficient "give" or flexibility as not to damage the finger if accidentally inserted into the housing when the propeller is being rotated. In addition, utilization of a flexible material will minimize the danger of any hair being snarled or wrapped around the propeller blade as it is rotated.

As best seen from FIG. 4, the drive means 16 includes the motor drive M which is preferably mounted on the front face or surface 25 of the housing with the drive shaft 30 projecting inwardly through a central opening, and the propeller blade 15 is fixed to the inner end of the drive shaft so as to afford sufficient clearance between the propeller and opposite plates 24 and 25 of the housing. A power cord 32 extends through a sleeve or sheath 34 affixed to and extending downwardly from the motor drive housing along the front surface of the face plate and continues into a control box 36. The control box has a carrying strap 37 and contains within its housing a battery pack represented at 38, an on/off switch 40 and a speed control 42. The speed control 42 may suitably be in the form of a rheostat or potentiometer and controlled to regulate the speed of the variable speed drive motor M thereby to regulate the speed of rotation of the propeller.

The modified form of invention shown in FIGS. 5 to 8 is comprised of a single face plate 44 having horizontally spaced openings 45 symmetrically disposed and spaced on opposite sides of a center drive shaft 47. The shaft 47 projects forwardly from a motor drive represented at M' mounted on the front surface of the plate 44 to drive a movable light control member in the form of a propeller 43. The motor drive M' is preferably a constant speed DC motor and is electrically connected by leads 48 to a suitable battery pack designated B which is releasably secured between a pivotal bracket 49 and stationary bracket 50 to the lower front face of the housing, as shown in more detail in FIGS. 7 and 8. The brackets 49 and 50 have contacts 49' and 50', and pivotal bracket 49 includes upper and lower clamps 52 to releasably retain a battery in place. This mounting eliminates the need for a separate on-off switch, since it is merely necessary to pivot the battery away from the bracket 50 to break the contact therebetween. However the speed of rotation of the drive shaft 47 can be varied or controlled by a braking element 54 which may simply consist of nothing more than a length of rubber or rubber-like material, such as, a rubber band member 55 having a looped end 56 disposed on the shaft 47 behind the propeller 43, and a string 58 is spliced to the lower free end of member 55, the string being enlarged as shown at the splice point so as to limit its movement upwardly into the housing. In this manner, by pulling the string downwardly the looped end 56 of the member 55 will generate sufficient frictional resistance to retard the speed of rotation of the drive shaft 47.

In the modified version shown in FIGS. 5 to 8, a head strap 60 is affixed to opposite sides of the face plate just above the eye openings and may suitably be an adjustable head strap which can be placed over the head so that rear cushion layers 62 rest against the forehead as described in connection with FIGS. 1 to 4. In each form, the cushion 22 or 62 is preferably composed of layers of flexible materials bonded together and of generally T-shaped configuration having an upper cross portion 63 adapted to rest upon the forehead and a relatively thick stem portion 64 extending downwardly between the eye openings and adapted to rest on the bridge of the nose. The cushion layers taper somewhat rearwardly so as to assure spacing of the housing or plate from the head of the wearer whereby to minimize the possibility of hair being drawn into the eye openings which could interfere with rotation of the propeller blade. Most desirably however the cushion is so mounted as to cause the device to be placed upon the face with the eye openings slightly above the eyes of the wearer and with the propeller and eye openings angled upwardly at a slight angle or degree. In this way, the head does not have to be tilted back to a great extent in order to align the device with the sun.

In the preferred form of invention, use of a remote control for the phosphene generator reduces the weight of the unit strapped to the head and also permits control from waist level so that it is not necessary to raise the arm to manipulate the controls on the unit. The carrying strap 37 also provides a means to permit more convenient and secure holding of the controls. In both forms, the propeller is preferably composed of a plastic, foam or other similar flexible lightweight material as an added safety feature and is sized in each case so as not to completely block the light passage through the eye openings at any time. Again, the propeller is preferably composed of a cellular plastic or foam material.

In the modified form shown in FIGS. 5 to 8, the battery holder is pivotal so that it also acts as the switch, although this arrangement could be replaced by a conventional battery holder with a separate electrical switch. If desired, various filters may be inserted in the eye openings, for example, to screen against ultraviolet rays. In addition, the front surface of the housing in the form shown in FIGS. 1 to 4 or the face plate shown in FIGS. 5 and 6 may be mirrored surfaces so as to minimize heating of the plate or housing. Enclosure of the propeller within a housing of course protects it from external factors such as wind and permits more accurate control through the motor drive or other drive source. On the other hand, use of a single plate reduces the weight and increases its portability and comfort.

The remote control device shown in FIGS. 1 to 4 may include a photocell in place of a battery as the speed control means so that the amount of light present will regulate energization of the motor, and a switch or potentiometer may be added to augment the photocell in controlling the rate of speed of the motor especially in dim light.

It will be further apparent from the foregoing descriptions of alternate forms of the present invention that the constant speed motor drive and brake control as illustrated in FIGS. 5 and 6 may be interchanged with the type of variable speed control described with reference to FIGS. 1 to 4.

Variable or various shaped propellers may be readily interchanged with the propellers as shown, and for instance this may be done in order to vary the wave form of light presented to the eye and to create modulations which will produce qualitatively unique variations in the phosphenes generated. In either form of invention as described, correlation of the shape and size of the propeller blades so as to occupy no more than a maximum of on the order of three-quarters of the eye openings at any time together with the variable speed control has been found to overcome the problem of flicker sickness to a great extent while maintaining the maximum average light intensity level. Generally, if the light is modulated within the frequency range of the Alpha, Pheta or Beta brain waves or within the range of the second harmonic thereof, flicker sickness is possible. At the same time, this is the same range of frequencies needed to produce phosphenes with a strobe light. Again however, by permitting some of the light to pass through at all times it has been discovered that when such a light is modulated within the frequency range indicated, the incidence of flicker sickness is greatly minimized. If a series of bright lights are repetitively flashed in front of the eye in which the light flashes are separated by complete darkness intervals, as is the case with strobed light, flicker sickness may result when the eyes are constantly exposed to this light over a time interval of any substantial duration on the order of several minutes. However, if the duration of darkness periods or pulses between the light pulses is substantially reduced and periods of complete darkness eliminated, flicker sickness is arrested.

A possible explanation as to why flicker sickness is diminished with this scheme relates to the known phenomena of evoked potentials, electro-anesthesia, and electro-convulsion. It has been shown that whenever a light or sound is presented to the appropriate sense organ an electrical waveform is induced in the brain. This is called an evoked potential. Thus, if a light is flashed at 10 cps, a 10 cps waveform called "induced Alpha" can be recorded in the brain with an EEG. It has also been shown that electro-convulsive behavior is produced by placing a pulse through the tissue. If the waveform is unchanged but raised above the DC axis so that it becomes a pulsing DC, electro-convulsion stops and electro-anesthesia ensues. A bright light on the eyes causes an increase in intraocular pressure. This may result in raising the apparent evoked signal up above the DC axis in some part of the brain responsible for the flicker sickness reaction. Nonetheless, experimentation has directly revealed the lack of predictable flicker sickness when modulated light is combined with a high intensity light and viewed with closed eyes. These two factors and their means of accomplishment is specifically related to this invention. Viewing a bright light with closed eyes increases pressure on the eyes, and the increased intraocular pressure caused by the bright light creates simultaneously a seemingly lessened flicker sickness reaction and increased phosphene production. The perceptual phenomena produced by the present invention are of interest both from a psychological and aesthetic standpoint. The variable capabilities of this invention increase the potential for pleasing and stimulating patterns of visual sensation. Used properly, the invention can be operated briefly or for a prolonged time for the entertainment of the user and endless varieties of images will be produced.

Apparatus within the scope of the present invention is adapted for use in achieving various novel visual effects through adjustment of the speed of operation of the light modulator and intensity of the light source, interrupted visual sequences and the like. For example, when actuated in the presence of a strong light source such as a high intensity light or the sun with the eyes of the user closed, a series of vividly colored flashes are seen, often accompanied by some of the patterns mentioned earlier. Viewing of an object with the eyes open produces colors superimposed on those objects viewed, patterns, and interrupted sequences representative of vintage motion pictures. The imagination of the user places the only limit upon an otherwise infinite variety of visual effects.

Color is a factor in maximizing phosphene generation. Bright yellow-orange light seems favorable over white light. Filters may be added to the eye openings or lenses to maximize the benefits of the color factor mentioned. When the phosphene generator is first used, the images will seem thrust within the mind's eye of the user but later after he gains experience, it becomes possible to actively manipulate the phosphenes in a creative way. The foam cushion which lies between the mask's rigid body and face of the user is designed to rest the pressure of the mask against the upper bridge of the nose and the middle lower forehead — between the eyebrows. With the cross-shaped foam pad the side of the face is open to view from the side. It is thus that the spots of sun on the closed eyes may be viewed by the instructor as a check against improper first time use. This open form also allows air to circulate for comfortable use in the sun. The same is true in the preferred form as described by inducing an air current through the vent holes. When a view of the user's eyes by the instructor or air circulation to the face is not necessary, the foam may surround the face of the user as with many conventional masks or goggles.

From the foregoing, it will be appreciated that the method and apparatus of the present invention affords an extremely reliable but simplified manner and means for producing phosphenes either for purposes of amusement or for eye exercising and other possible therapeutical effects. It is therefore to be understood that various modifications and changes may be resorted to both with respect to the method and apparatus of the present invention without departing from the spirit and scope thereof.

What is claimed is:

1. In a phosphene generator device adapted to be worn on the head of a person wherein openings are provided therein in spaced relation to one another so as to be aligned with the eyes whereby to pass light from an external light source to the eyes, the improvement comprising:

a movable element mounted on said device so as to traverse the eye openings, said movable element having blade members passing over the eye openings of a size so as not to completely block the passage of light through the eye openings, and variable speed drive means to impart movement to said movable element at a predetermined but variable rate of speed in order to produce light pulses in the range of 1 to 25 cycles per second.

2. In a phosphene generator according to claim 1, said movable element being in the form of a rotatable propeller centered with respect to the eye openings, and said variable speed drive means being in the form of rotatable drive means to impart rotation to said propeller at a variable rate of speed.

3. In a phosphene generator according to claim 1, wherein said movable element is in the form of a rotatable propeller having blade members movable past the eye openings, said variable speed drive means defined by a constant speed motor including a drive shaft to which said propeller is affixed, and a braking member on said drive shaft to impart frictional resistance to rotation of said drive shaft in controlling the speed or rotation of said propeller.

4. In a phosphene generator device according to claim 3, said braking member being defined by a looped portion composed of rubber or rubber-like material in surrounding relation to said drive shaft and a hand-engaging portion connected to said looped portion to apply frictional pressure thereto.

5. In a phosphene generator according to claim 4, in which said flexible looped portion and hand-engaging portion are defined by a rubber band having a closed end passing over said drive shaft.

6. In a phosphene generator device according to claim 1, said movable element defined by a rotatable propeller centered with respect to the eye openings, said propeller having blade members passing over the eye openings of a size so as not to completely block the passage of light therethrough, and said variable speed drive means is defined by a variable speed drive motor mounted in front of said propeller and including a drive shaft to which said propeller is affixed, and a power source for said motor drive being defined by a battery mount releasably attached to said device.

7. A phosphene generator device comprising in combination:

a housing having front and rear generally circular plates interconnected in spaced parallel relation to one another, said front and rear plates provided with aligned eye openings in each of said plates whereby when the housing is mounted on the head of a person the eye openings in said plates are aligned with the eyes;

an external light source;

a rotary element mounted in said housing for rotation about an axis parallel to the path of light through said eye openings, said rotary element being sized in relation to said eye openings so as to present alternating light and dark pulses; and variable speed rotating means drivingly connected to said rotating element to impart rotation to said element at a predetermined rate of speed.

8. A phosphene generator according to claim 7, said rotating element being sized so as not to completely block the passage of light through the eye openings in passing over the eye openings, and said variable speed rotating means cooperating with said rotating element whereby to rotate said element at a rate such that the duration of light pulses exceed the duration of dark pulses whereby to maximize the average intensity of light passing through the eye openings.

9. A phosphene generator device according to claim 7, said rotating element being in the form of a propeller being centered for rotation in said housing and having propeller blades traversing said eye openings, said propeller blades being of a size so as not to completely block the passage of light through the eye openings at any given time.

10. A phosphene generator device according to claim 9, at least the eye openings in one of said plates being provided with filter means to cooperate with said propeller in modulating and controlling the intensity and bandwidth of light passing through said eye openings.

11. A phosphene generator device according to claim 8, said rotating element defined by a propeller centered for rotation within said housing and said variable speed rotating means being defined by a variable speed drive motor mounted on the front circular plate of said housing and having a drive shaft projecting rearwardly therethrough for driving connection to the center of said propeller, and speed control means for said variable speed drive means operative to control rotation of said propeller to produce light pulses in the range of 1 to 25 cycles per second.

* * * * *